United States Patent
Prasad et al.

(10) Patent No.: US 10,192,307 B2
(45) Date of Patent: Jan. 29, 2019

(54) SYSTEM AND METHOD FOR EXTRACTING A PERIODIC SIGNAL FROM VIDEO

(71) Applicant: Xerox Corporation, Norwalk, CT (US)

(72) Inventors: Prathosh A. Prasad, Karnataka (IN); Sanjay Bharadwaj, Karnataka (IN); Pragathi Praveena, Karnataka (IN); Tejaskumar Dipaklal Bengali, Karnataka (IN); Satish Prasad Rath, Karnataka (IN); Himanshu Jayantkumar Madhu, Maharashtra (IN)

(73) Assignee: Xerox Corporation, Norwalk, CT (US)

( * ) Notice: Subject to any disclaimer, the term of this patent is extended or adjusted under 35 U.S.C. 154(b) by 187 days.

(21) Appl. No.: 15/336,475

(22) Filed: Oct. 27, 2016

(65) Prior Publication Data
US 2018/0122066 A1    May 3, 2018

(51) Int. Cl.
| | |
|---|---|
| G06K 9/00 | (2006.01) |
| G06T 7/00 | (2017.01) |
| G06T 7/20 | (2017.01) |
| G06T 5/00 | (2006.01) |
| A61B 5/00 | (2006.01) |

(Continued)

(52) U.S. Cl.
CPC .......... *G06T 7/0012* (2013.01); *A61B 5/0022* (2013.01); *A61B 5/0077* (2013.01); *A61B 5/024* (2013.01); *A61B 5/08* (2013.01); *A61B 5/1102* (2013.01); *A61B 5/113* (2013.01); *A61B 5/1128* (2013.01); *A61B 5/742* (2013.01); *G06T 5/002* (2013.01); *G06T 7/2033* (2013.01); *G06T 2207/10016* (2013.01); *G06T 2207/20024* (2013.01); *G06T 2207/30048* (2013.01)

(58) Field of Classification Search
None
See application file for complete search history.

(56) References Cited

U.S. PATENT DOCUMENTS

| | | |
|---|---|---|
| 7,415,164 B2 | 8/2008 | Wren et al. |
| 8,553,940 B2 | 10/2013 | Kirenko et al. |

(Continued)

OTHER PUBLICATIONS

Briassouli, A., et al., "Extraction and Analysis of Multiple Periodic Motions in Video Sequences", IEEE Transactions on Pattern Analysis and Machine Intelligence, Jul. 2007, pp. 1244-1261, vol. 29, No. 7.

(Continued)

*Primary Examiner* — Stephen P Coleman
(74) *Attorney, Agent, or Firm* — Philip E. Blair; Fleit Gibbons Gutman Bongini & Bianco P.L.

(57) ABSTRACT

What is disclosed is a system and method for processing a video to extract a periodic signal which was captured by the video imaging device. One embodiment involves the following. First, a video of a subject in a scene is received. The video is acquired by a video imaging device. There is an underlying motion signal in the scene corresponding to cardiac or respiratory function. A time-series signal is generated for each pixel or for each group of pixels in a temporal direction across a plurality of image frames. Time-series signals of interest are selected. The selected time-series signals of interest are then processed to obtain a periodic signal corresponding to cardiac or respiratory function. The present method has a low computational complexity, is robust in the presence of noise, and finds its uses in applications requiring real-time motion quantification of a signal in a video.

7 Claims, 4 Drawing Sheets

(51) Int. Cl.
  *A61B 5/024* (2006.01)
  *A61B 5/08* (2006.01)
  *A61B 5/11* (2006.01)
  *A61B 5/113* (2006.01)

(56) References Cited

U.S. PATENT DOCUMENTS

| | | |
|---|---|---|
| 8,600,213 B2 | 12/2013 | Mestha et al. |
| 8,897,522 B2 | 11/2014 | Mestha et al. |
| 2008/0317129 A1 | 12/2008 | Lertrattanapanich et al. |
| 2009/0187112 A1 | 7/2009 | Meir et al. |
| 2014/0086452 A1 | 3/2014 | Ukil et al. |
| 2014/0241626 A1 | 8/2014 | Sull et al. |

OTHER PUBLICATIONS

Cutler, R., et al., "Robust Real-Time Periodic Motion Detection, Analysis, and Applications", IEEE Transactions on Pattern Analysis and Machine Intelligence, Aug. 2000, pp. 781-796, vol. 22, No. 8.

SYSTEM AND METHOD FOR EXTRACTING A PERIODIC SIGNAL FROM VIDEO

TECHNICAL FIELD

The present invention is directed to systems and methods for processing a video to extract a periodic signal that corresponds to cardiac or respiratory function.

BACKGROUND

Simultaneous capture of motion information in a video can provide valuable information in many applications such as, for example, biometrics where a detectable brainwave signal or some repetitive physical motion such as eye blinks, twitches, ticks, and the like, is desired to be extracted from the video. Another application is video-based traffic enforcement where a signal relating to tire rotational speed is desired to be measured. In healthcare, the ability to monitor patient physiological function by non-contact means is highly desirable in monitoring, for example, neonatal patients, burn or trauma patients, sleep studies, and other cases where a continuous measurement of a patient physiological signal is required without the use of adhesive patches, clips, straps, and the like, which may be impractical or lead to patient discomfort, dependency, loss of dignity, and further may fail due to wires coming lose or moving. The teachings hereof are directed to extracting a periodic signal from a video of a scene.

BRIEF SUMMARY

What is disclosed is a system and method for extracting a periodic signal from a video. Each spatial location in the field of view of the camera capturing the video is modeled as a noise-corrupted Linear Time-Invariant (LTI) System with unknown system dynamics. Such a system is a single-input multiple-output (SIMO) system where a single generating signal drives a plurality of LTI responses. The present invention estimates a periodic signal through a process of aggregating selected time-series signals generated by each pixel's respective LTI channel. One embodiment hereof involves receiving a video of a scene which has an underlying motion signal g(t) generated by respiration. A time-series signal is generated for each pixel or for each group of pixels across a plurality of image frames. Time-series signals of interest are selected based on any of: an amount of positive correlation between signals, a signal-to-noise ratio as compared to a threshold, and/or features associated with the time-series signals. In a manner more fully disclosed herein, the selected time-series signals are aggregated to obtain a periodic signal ĝ(t). The estimated periodic signal is utilized for patient cardiac or respiratory function assessment. The methods disclosed herein have a low computational complexity, are robust in the presence of noise, and find their uses in a wide array of applications requiring real-time quantification of a motion signal embedded in a video.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for extracting an estimated periodic signal from a video.

Non-Limiting Definitions

A "subject" refers to a living being. Although the term "human" or "patient" may be used throughout this text, it should be appreciated that the subject may be something other than a human such as, for instance, a primate. As such, the use of "human", "person" or "patient" is not to be viewed as limiting the scope of the appended claims strictly to human beings.

A "video", as is generally understood, comprises a time-varying sequence of image frames. Each image frame has a height H in pixels and a width W in pixels. The video may be pre-processed to compensate for motion induced blur, imaging blur, slow illuminant variation, to enhance contrast or brightness, or to reduce or eliminate camera-related noise or environmental factors.

Figure 1:
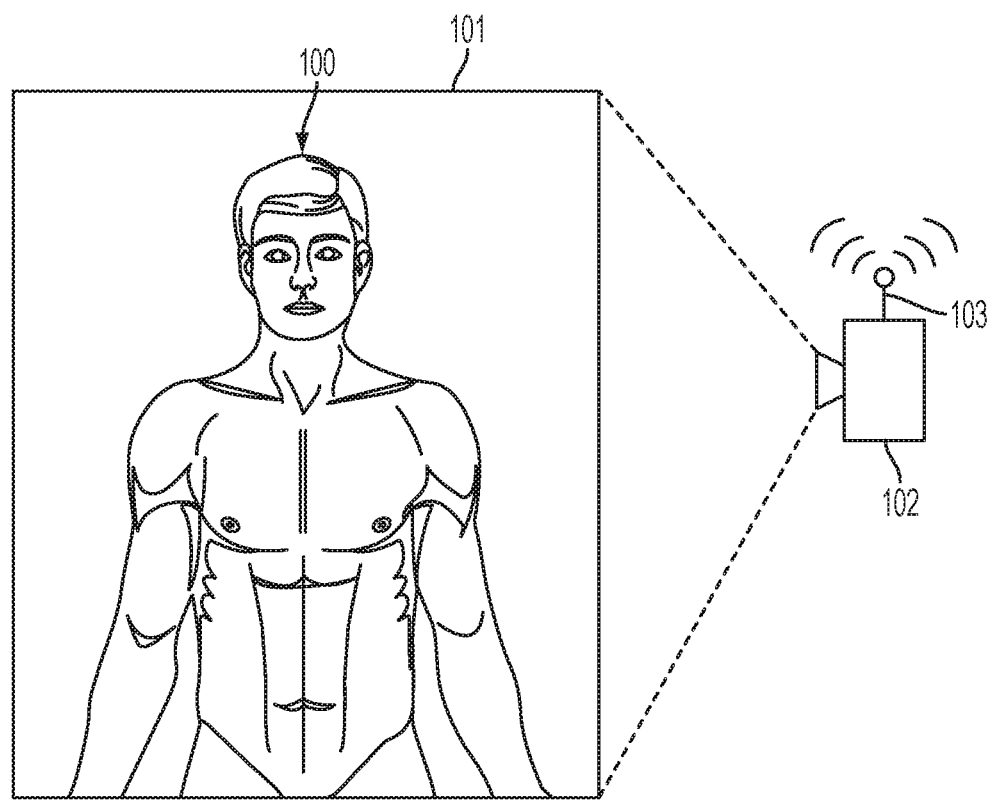
FIG. 1 shows an example video image device capturing time-sequential image frames of a scene containing a male subject.
Figure 2:
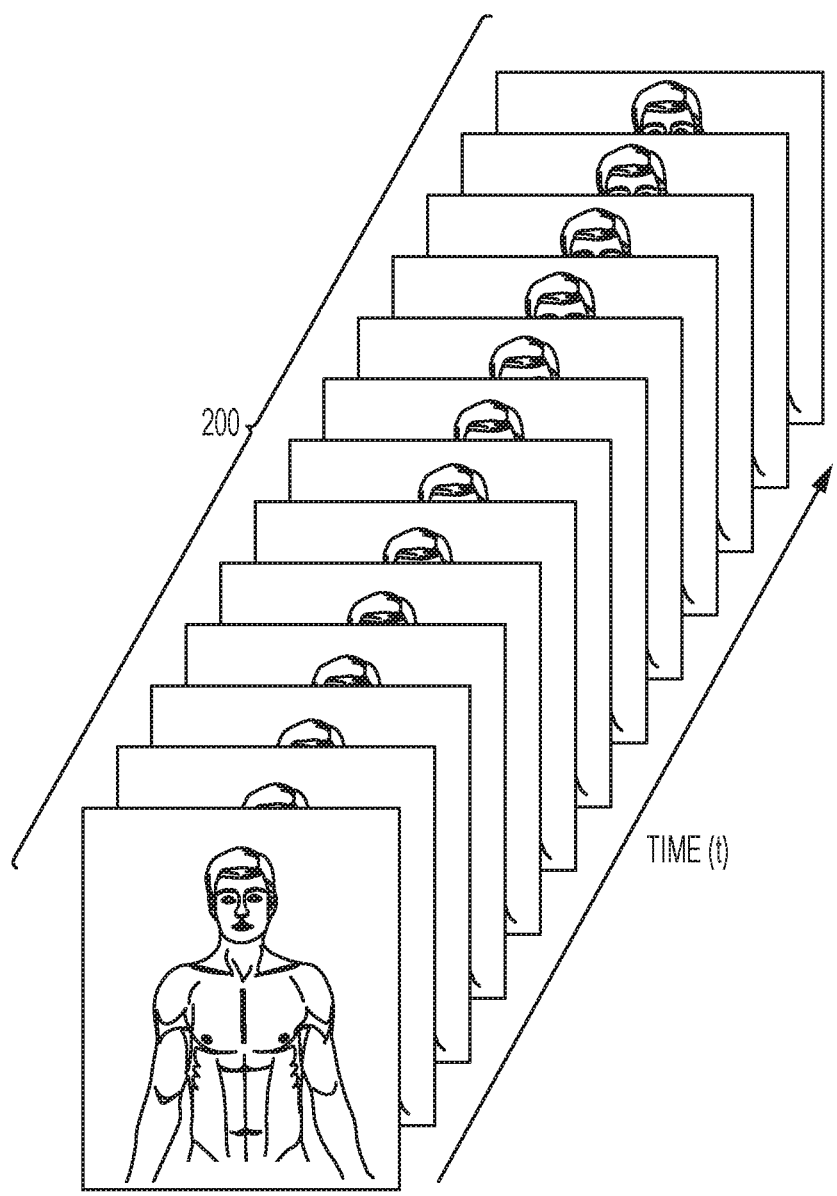
FIG. 2 shows an example plurality of time-sequential image frames acquired by the video imaging device of FIG. 1.

A "video imaging device" refers to a device for acquiring a video. FIG. 1 shows an example video imaging device 102 acquiring video 101 of a subject 100 in a scene. Image frames of the video may be communicated to a remote device via a wireless communication element 103, shown as an antenna. FIG. 2 shows an example plurality of time-sequential image frames (collectively at 200) acquired over time t by the video imaging device 102 of FIG. 1. It should be understood that the number of image frames in FIG. 2 is illustrative and should not be viewed as limiting the scope of the appended claims to the type or amount of image frames shown. The video imaging device has at least one lens that focuses energy from objects in a scene onto an array of specialized sensors which convert that detected energy into electrical signals on a per-pixel basis. The video device outputs an array of pixels each having an intensity value corresponding to the energy measured at that pixel location in the scene. The video imaging device may be a monochrome video camera for capturing black/white images, or a color video camera for capturing color values of pixels corresponding generally to the primary visible colors (typically RGB). The video imaging device can also be a multi-spectral or a hyperspectral video imaging device. Such devices have a relatively low frame rate and low spatial resolution but high spectral resolution. The video device may be a hybrid device capable of operating in dual modes, i.e., a conventional video mode with high frame rate and high spatial resolution, and a spectral mode with high spectral resolution. The video imaging device can be a thermal video camera with specialized sensors which convert infrared energy into electrical signals and outputs a thermal image comprising an array of pixels with color values corresponding to surface temperatures of the objects in the image across a pre-defined thermal wavelength band. The thermal imaging system can be any of: a single-band or multi-band infrared camera operating in the thermal range, or a hyperspectral infrared camera operating in the thermal range. The video imaging device may include at least one processor executing machine readable program instructions for analyzing video images to extract a periodic signal therefrom in accordance with the methods disclosed herein. Video imaging devices comprising standard equipment and those with specialized sensors are available from a wide array of vendors in various streams of commerce. The image frames of the video are processed in a temporal direction to obtain a time-series signal for each pixel or for each group of pixels combined by averaging or summation.

A "time-series signal" is a signal which contains frequency components that relate to motion occurring in the scene that was captured in the video. Essentially, the scene in the image frames is modeled as a bounded input bounded output (BIRO) stable, minimum phase, Linear Time-Invariant (LTI) system wherein a multiplicity of LTI channels (outputs) are all driven by the same (input) signal. In such a manner, the $i^{th}$ time-series signal associated with the $i^{th}$ pixel (or $i^{th}$ group of pixels) can be given by:

$$x_i(t) = h_i(t) \otimes g(t) + n_i(t) \quad (1)$$

where $n_i(t)$ is a noise associated with the $i^{th}$ pixel, $h_i(t)$ is a transfer function of the LTI channel associated with the $i^{th}$ pixel, $\otimes$ is a convolution operator, and $1 \leq i \leq HW$. This is solved by a blind deconvolution technique as is generally understood in the arts. The reader is directed to the texts: "*Blind Deconvolution*", Prentice-Hall (1994), ISBN-13: 978-0130873620, and "*Unsupervised Adaptive Filtering Volume 2: Blind Deconvolution*", Wiley-Interscience (2000), ISBN-13: 978-0471379416, both of which are incorporated herein in their entirety by reference. Further, the well-known multi-paradigm numerical computing environment known as MATLAB has algorithms for performing various aspects of multi-channel blind deconvolution. A subset of the generated time-series signals are selected.

"Selecting time-series signals" means to identify time-series signals of interest to obtain a set $X^+$ of selected signals. In one embodiment, the signals of interest are selected because they are positively correlated. A perfectly correlation means that a relationship exists between two parameters 100% of the time. In another embodiment, signals of interest are selected based on a signal-to-noise ratio (SNR) as given by:

$$P = \lim_{T \to \infty} \frac{1}{2T} \int_{-T}^{T} x(t)^2 dt \quad (2)$$

$$SNR = \frac{P_{sig}}{P} \quad (3)$$

where $P_{sig}$ is the power of the signal in a band of interest and P is the total power over time interval $[-T, T]$. The SNR is compared to a threshold level. It should be appreciated that the threshold will likely vary from application to application (and likely from patient to patient) and therefore a discussion as to a specific threshold value is omitted. In healthcare applications, the threshold can based on historical data or patient health vitals such as: cardiac rate, blood pressure, respiration rate, and signals from electrocardiogram (ECG/EKG) and electroencephalogram (EEG) devices. Moreover, a user, technician, or professional may use a mouse or a touchscreen display to pre-set or otherwise select a threshold. The threshold may be dynamically adjusted. In yet another embodiment, features are used for time-series signal selection purposes. Features include, for example, coefficients of a quadratic polynomial fit to one or more signal segments of the time-series signal or to a reference signal. Features may comprise eigen features, coefficients of a filter, coefficients of a discrete cosine transform, coefficients of a wavelet transform of the signal, a standard deviation of the signal, a root mean square of the signal, a norm of the signal, values at peaks/valleys and/or the interval between peaks or valleys of a signal, and may also include pixel location in the image frame and motion component information such as amount of pixel movement between image frames. Other features may be obtained from a deep learning algorithm. Pixels in a region of interest in a given scene may be grouped and their mean, median, standard deviation, or higher order statistics computed and any of these used as features. Features of time-series signals may be clustered using a clustering technique. Methods for forming clustering include: K-means testing, vector quantization (such as the Linde-Buzo-Gray algorithm), constrained clustering, fuzzy clustering, nearest neighbor, linear discriminant analysis, Gaussian Mixture Model, and a support vector machine, as are understood in the arts. The clustering may be supervised or unsupervised. A distance metric can be utilized to select a cluster. Such metrics include, for example, a center of the cluster, a boundary of the cluster, or a weighted sum of at least some features in the cluster. A distance can be Euclidean, Mahalanobis, Bhattacharyya, Hamming, or Hellinger. A user may manually select one or more clusters. The selected time-series signals of interest in set $X^+$ are aggregated.

"Aggregating time-series signals" means to process the selected time-series signals of interest in set V to generate the desired estimated periodic signal $\hat{g}(t)$. It should be appreciated that, when the motion in the scene is a small single frequency sinusoid, an average of the selected signals over $X^+$ asymptotically converges to an amplitude-scaled version of the underlying motion signal, i.e., $\hat{g}(t) \cong cg(t)$. As such, the selected time-series signals of interest can be aggregated using the following:

$$\hat{g}(t) = \frac{1}{\overline{X^+}} \sum_{i \in X^+} x_i(t) \cong cg(t) \quad (4)$$

where $\overline{X^+}$ denotes cardinality of $X^+$. In one embodiment, the generated estimated periodic signal is further processed to obtain a physiological signal.

A "physiological signal" is a signal containing meaningful frequencies that correspond to cardiac or respiratory function. A bandpass filter with a low cut-off frequency $f_c - f_w$ and a high cut-off frequency $f_c + f_w$ can be used to extract a physiological signal from the estimated periodic signal, where $f_c$ is a frequency of interest and $f_w$ is the bandwidth. For cardiac signal extraction, $f_c$ can be obtained from the subject's cardiac pulse with $f_w$ in the range of 0.2-0.3 Hz depending on the subject's cardiac health. For infants, a wider bandwidth should be used. For respiratory signal extraction, $f_c$ can be obtained can be obtained from the subject's tidal breathing. In adults, tidal breathing is typically between 12 to 16 cycles per minute with a bandwidth of 2 to 4 cycles per minute around $f_c$, depending on the subject's respiratory health.

"Receiving image frames" is intended to be widely construed and includes: retrieving, capturing, acquiring, or otherwise obtaining video for processing in accordance with the teachings hereof. Video can be retrieved from a memory or storage device of the video imaging device or retrieved from a media such as a CDROM or DVD. Video can be obtained from a remote device over a network or downloaded from a web-based system or application which makes video available for processing. The received video may be pre-processed to identify regions of interest in the image frames where the periodic signal is likely to be found such as, for example, a region of exposed skin of a subject in the video. A region of interest can be identified in the image frames using image processing techniques which include, for example, color and texture identification, object identification, spatial feature analysis, spectral information, pattern recognition, and facial recognition. A user or technician may use a mouse or, for instance, a touchscreen display to identify regions of interest in the image frames.

A "storage device" refers to a device or system for storing data, images, formulae, machine readable program instructions, and the like. Storage devices include RAM, ROM, Memory, CD-ROM, DVD, flash drives, hard drives, and other volatile or non-volatile media.

A "display device" refers to any device capable of receiving a signal for visual display. Display devices include, for example, LCD, HD, CRT, and touchscreen displays, as are commonly understood. Such devices have one or more processors which operate in conjunction with specialized memory.

It should be appreciated that the steps of: "receiving", "extracting", "generating", "selecting", "averaging", "clustering", "determining", "performing", "filtering", "smoothing", and the like, as used herein, include the application of any of a variety of signal processing techniques as are known in the signal processing arts, as well as a variety of mathematical operations according to any specific context or for any specific purpose. It should be appreciated that such steps may be facilitated or otherwise effectuated by a microprocessor executing machine readable program instructions.

Example Flow Diagram

Figure 3:
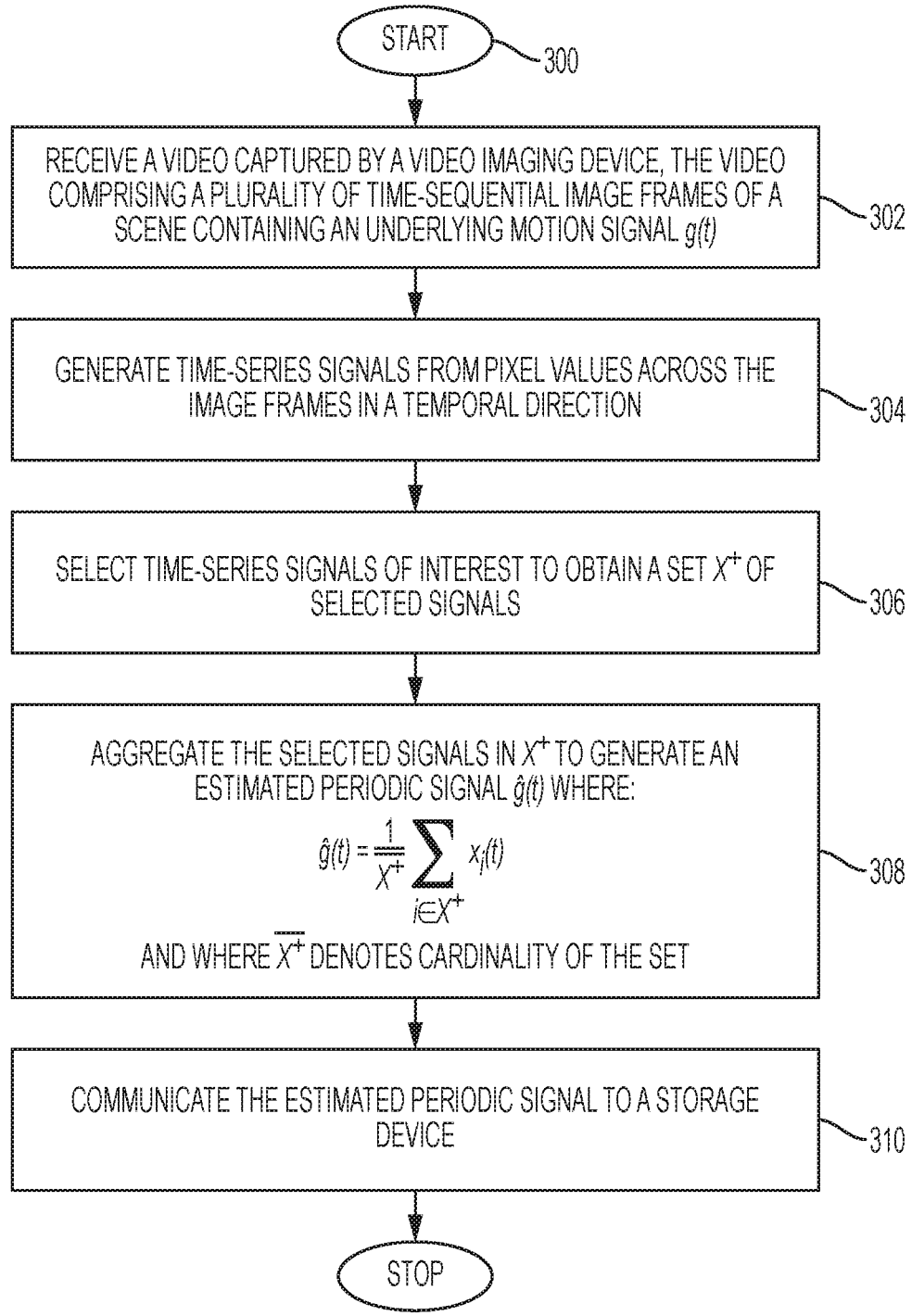
FIG. 3 is a flow diagram which illustrates one example embodiment of the present method for extracting an estimated periodic signal from a video.

Reference is now being made to the flow diagram of FIG. 3 which illustrates one example embodiment of the present method for extracting an estimated periodic signal from a video. Flow processing begins at step 300 and immediately proceeds to step 302.

At step 302, receive a video captured by a video imaging device, the video comprising a plurality of time-sequential image frames of a scene containing an underlying motion signal g(t).

At step 304, generate time-series signals from pixel values across the image frames in a temporal direction.

At step 306, select time-series signals of interest to obtain a set $X^+$ of selected signals.

At step 308, aggregate the selected signals in $X^+$ to generate an estimated periodic signal ĝ(t).

At step 310, communicate the estimated periodic signal to a storage device. In this embodiment, further processing steps. In those embodiments where the obtained estimated periodic signal is a physiological signal associated with cardiac function, the signal is used to determine an occurrence of any of: cardiac arrhythmia, cardiac stress, cardiac failure, and cardiac disease. In those embodiments where the obtained estimated periodic signal is a physiological signal associated with respiratory function, the signal is used to determine an occurrence of any of: respiratory distress, respiratory failure, pulmonary disease, and sudden infant death syndrome.

It should be appreciated that the flow diagrams depicted herein are illustrative. One or more of the operations in the flow diagrams may be performed in a differing order. Other operations may be added, modified, enhanced, or consolidated. Variations thereof are intended to fall within the scope of the appended claims.

Block Diagram of Video Processing System

Figure 4:
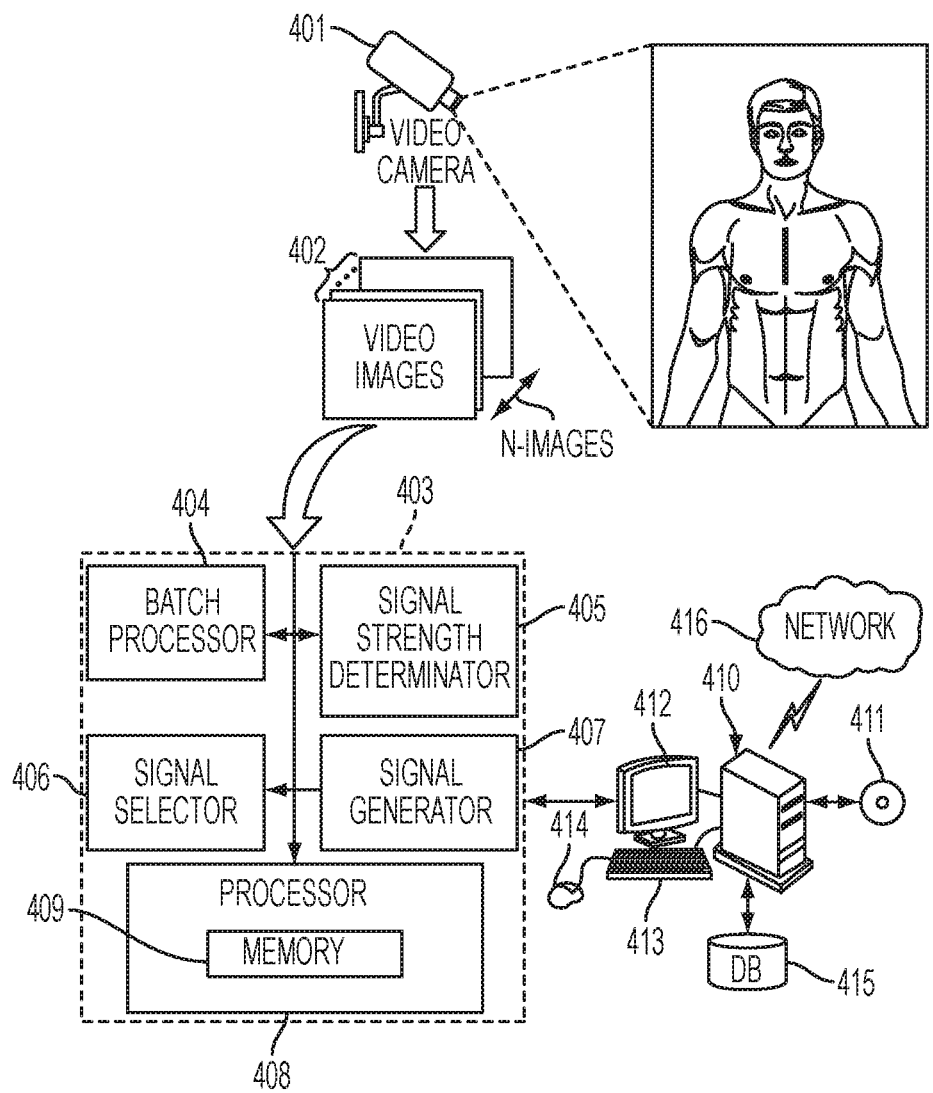
FIG. 4 illustrates a functional block diagram of one example video processing system for extracting an estimated periodic signal from a video as shown and described with respect to the flow diagram of FIG. 3.

Reference is now being made to FIG. 4 which illustrates a block diagram of one example video processing system 400 for extracting an estimated periodic signal from a video, as described with respect to the flow diagram of FIG. 3.

In FIG. 4, the video imaging device 401 is shown acquiring video of the subject of FIG. 1. The image frames comprising the video (collective at 402) are communicated to the video processing system 403. Batch Processor 404 receives the time-sequential image frames and processes pixels associated with the body region in the image frames to obtain time-series signals on a per-pixel basis. Signal Strength Determinator 405 receives the time-series signals and proceeds to calculate a signal-to-noise ratio for each signal. In another embodiment, Module 405 extracts features and performs clustering. Signal Selector 406 receives the calculated SNRs and selects time-series signals that are positively correlated and which have a highest signal strength. In another embodiment, Selector 406 selects one or more clusters. Signal Generator 407 receives the set $X^+$ containing the selected time-series signals of interest from Selector 406 and proceeds generate the estimated periodic signal using the methods disclosed herein. Processor 408 executes machine readable program instructions operating alone or in conjunction with other processors and Memory 409, to assist or otherwise perform the functionality of any of the modules or processing units of the video processing system 403. Processor 409 further facilitates communication with the workstation 410.

The video processing system of FIG. 4 is shown in communication with a workstation comprising, at least in part, a computer case which houses various components such as a motherboard with a processor and memory, a network card, a video card, a hard drive capable of reading/writing to machine readable media 411 such as a floppy disk, optical disk, CD-ROM, DVD, magnetic tape, and the like, and other software and hardware needed to perform the functionality of a computer system. The workstation further includes a display device 412, such as a CRT, LCD, or touchscreen device, for displaying information, video, measurement data, computed values, medical information, results, locations, and the like. A user can view any of that information and make a selection from menu options displayed thereon. The keyboard 413 and mouse 414 effectuate a user input or selection. The workstation implements a database in storage device 415 wherein records are stored, manipulated, and retrieved in response to a query. Such records, in various embodiments, take the form of patient medical histories. Although the database is shown as an external device, the database may be internal to the workstation mounted, for example, on a hard disk within the computer case.

It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing image frames to obtain time-series signals and to generate an estimated periodic signal as disclosed herein. The workstation is further enabled to display image frames of the video. A user or technician may use the workstation to identify regions of interest, set parameters, select image frames and/or regions of interest for processing. Such user entries may be stored/retrieved in a storage devices 411 and 415 along with default settings, initial parameter values, and the like. A user may adjust various parameters employed or dynamic settings in real-time as successive batches of image frames are processed.

Although shown as a desktop computer, it should be appreciated that the workstation can be a laptop, mainframe, or a special purpose computer such as an ASIC, circuit, or the like. The embodiment of the workstation of FIG. 4 is illustrative and may include other functionality known in the arts. Any of the components of the workstation may be placed in communication with the video processing system 403 or any devices in communication therewith. Moreover, any of the modules and processing units of system 403 can be placed in communication with storage devices 412 and/or 415 and may store/retrieve therefrom data, variables, records, parameters, functions, and/or machine readable/executable program instructions, as needed to perform their intended functionality. Each of the modules of the video processing system of FIG. 4 may be placed in communication with one or more remote devices over a network 416. It should be appreciated that some or all of the functionality performed by any of the modules or processing units of system 403 can be performed, in whole or in part, by the workstation placed in communication with the video imaging device 401 over network 416. The embodiment shown is illustrative and should not be viewed as limiting the scope of the appended claims strictly to that configuration.

The teachings hereof can be implemented in hardware or software using any known or later developed systems, structures, devices, and/or software by those skilled in the applicable art without undue experimentation from the functional description provided herein with a general knowledge of the relevant arts. Various modules may designate one or more components which may, in turn, comprise software and/or hardware designed to perform the intended function. One or more aspects of the methods described herein are intended to be incorporated in an article of manufacture which may be shipped, sold, leased, or otherwise provided separately either alone or as part of a product suite or a service.

It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims.

What is claimed is:

1. A video processing system for processing a video of a subject in a scene for patient cardiac or respiratory function assessment, the video being captured by a video imaging device, the captured video being a plurality of time-sequential image frames containing an underlying motion signal g(t) desired to be extracted from the video, the video imaging device communicating the time-sequential image frames to a video processing system comprising:

a Batch Processor for receiving the time-sequential image frames and processing pixel values associated with a body region of the subject in the scene to obtain time-series signals, the pixel values being processed across the time-sequential image frames in a temporal direction;

a Signal Selector for selecting time-series signals of interest to obtain a set X+ of selected signals, wherein the time-series signals are selected by any of:

the Signal Selector receiving signal-to-noise ratios calculated by a Signal Strength Determinator, the Signal Selector selecting time-series signals of interest based on the determined signal-to-noise ratios as compared to a threshold; and the Signal Selector selecting time-series signals of interest based on an amount of positive correlation between time-series signals;

a Signal Generator for aggregating the selected time-series signals in $X^+$ and generating, as output to a memory, an estimated periodic signal $\hat{g}(t)$, where $\hat{g}(t) \cong cg(t)$ and c is an amplitude scaling factor, and wherein the estimated periodic signal corresponds to one of: cardiac or respiratory function; and a processor for retrieving the estimated periodic signal from the memory, and communicating the retrieved estimated periodic signal to a display device.

2. The video processing system of claim 1, wherein the Signal Selector comprises a workstation wherein a user selects time-series signals of interest based on features associated with the time-series signals.

3. The video processing system of claim 1, wherein the video imaging device is any of: a color video camera, a monochrome video camera, a thermal imaging system, a multispectral video imaging device, a hyperspectral video imaging device, and a hybrid device comprising any combination hereof.

4. The video processing system of claim 1, further comprising communicating the estimated periodic signal to any of: a storage device, and a remote device over a network.

5. The video processing system of claim 1, wherein the video is a streaming video and the estimated periodic signal is generated in real-time.

6. The video processing system of claim 1, wherein the $i^{th}$ signal associated with the $i^{th}$ pixel comprises:

$$x_i(t) = h_i(t) \otimes g(t) + n_i(t)$$

where $n_i(t)$ is a noise associated with the $i^{th}$ pixel, $h_i(t)$ is a transfer function of a linear time-invariant (LTI) channel associated with the $i^{th}$ pixel, $\otimes$ is a convolution operator, and $1 < i < HW$, each image frame comprising H×W pixels where H is the height of an image frame in pixels and W is the width of the image frame in pixels.

7. The video processing system of claim 6, wherein the estimated periodic signal $\hat{g}(t)$ comprises:

$$\hat{g}(t) = \frac{1}{\overline{X^+}} \sum_{i \in X^+} x_i(t)$$

where $\overline{X^+}$ denotes cardinality of the set.

* * * * *